United States Patent [19]

Martin

[11] 4,353,243

[45] Oct. 12, 1982

[54] FLEXIBLE DIAPHRAGM CONTROLLED VALVE

[75] Inventor: Archer J. P. Martin, Lausanne, Switzerland

[73] Assignee: Quadrex Corporation, Woodbridge, Conn.

[21] Appl. No.: 230,817

[22] Filed: Feb. 2, 1981

[51] Int. Cl.³ ............................................. G01N 31/08
[52] U.S. Cl. .................................. 73/23.1; 73/863.71; 137/877; 137/885; 251/61.1
[58] Field of Search ............... 137/863, 869, 877, 885; 251/61.1; 73/863.71, 863.72, 863.73, 23.1

[56] References Cited

U.S. PATENT DOCUMENTS

| | | | |
|---|---|---|---|
| 3,139,755 | 7/1964 | Reinecke et al. | 73/863.71 |
| 3,156,157 | 11/1964 | Smith et al. | 137/863 X |
| 3,767,161 | 10/1973 | Blatter | 251/61.1 |
| 4,119,120 | 10/1978 | Mehaffy et al. | 137/885 |
| 4,168,724 | 9/1979 | Graffunder et al. | 251/61.1 X |

FOREIGN PATENT DOCUMENTS

| | | | |
|---|---|---|---|
| 2821801 | 4/1980 | Fed. Rep. of Germany | 137/869 |
| 977364 | 12/1964 | United Kingdom | |
| 248329 | 12/1969 | U.S.S.R. | 251/61.1 |
| 458681 | 2/1975 | U.S.S.R. | 251/61.1 |

*Primary Examiner*—Gerald A. Michalsky

[57] ABSTRACT

A multiport flexible diaphragm controlled valve is disclosed. The parts are all interconnected by low dead volume channels. The valve provides extremely fast response times, no moving parts other than the control diaphragm, operability over a wide range of operating conditions including high temperatures and is adaptable to use with all types of chromatography systems. The valve may also be utilized in a double sided configuration enabling two independent flow patterns to coexist simultaneously and be switched totally independent of one another.

7 Claims, 11 Drawing Figures

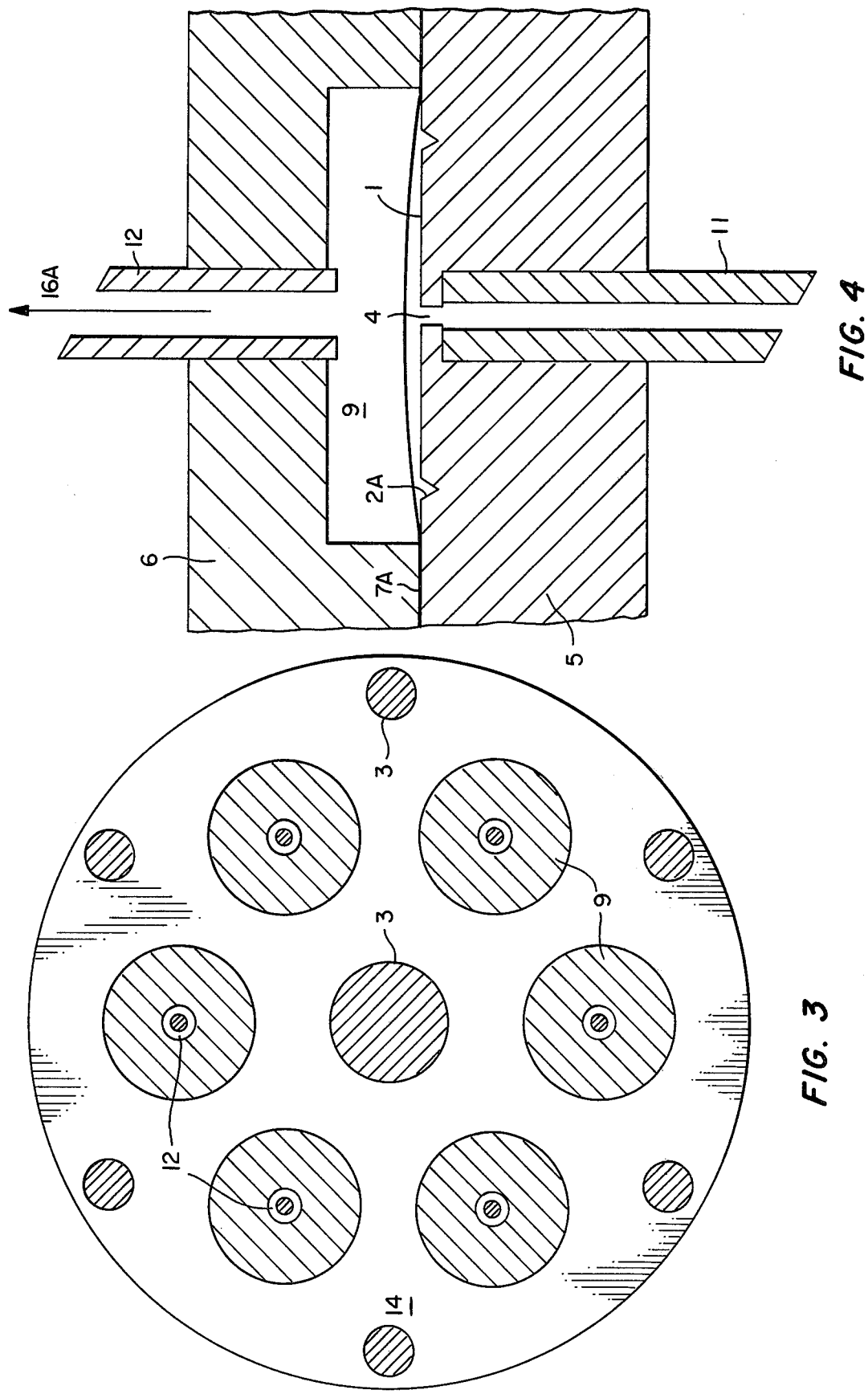

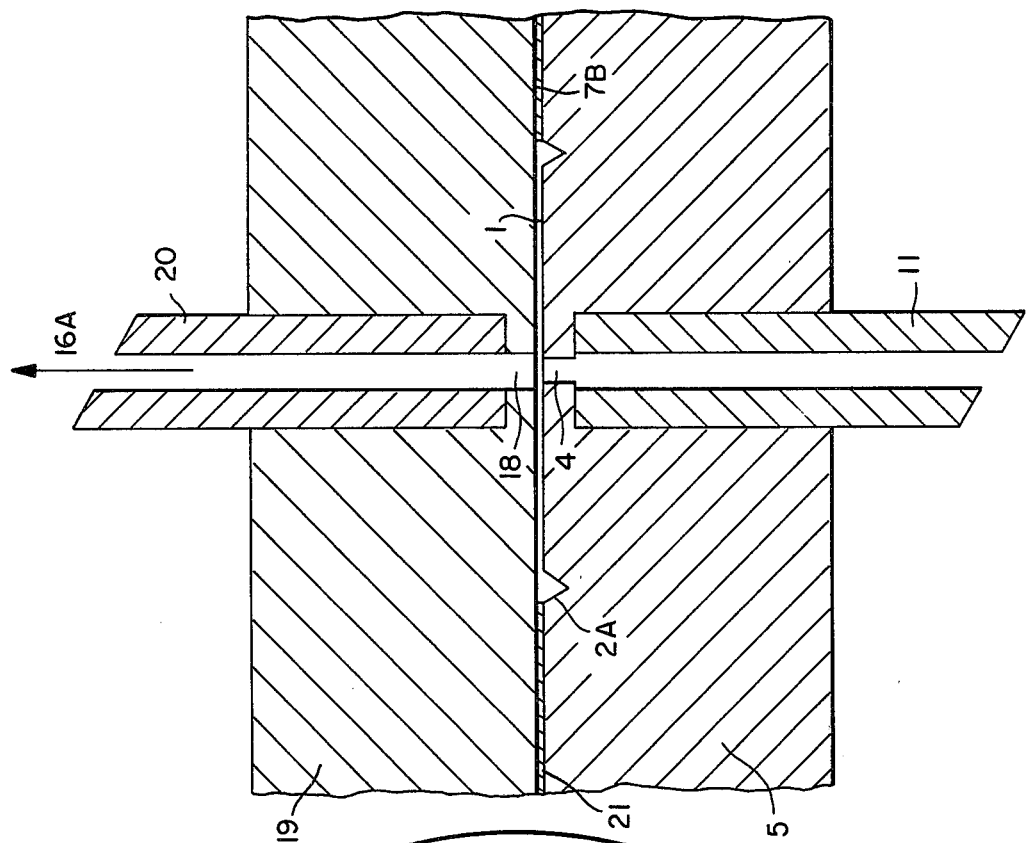
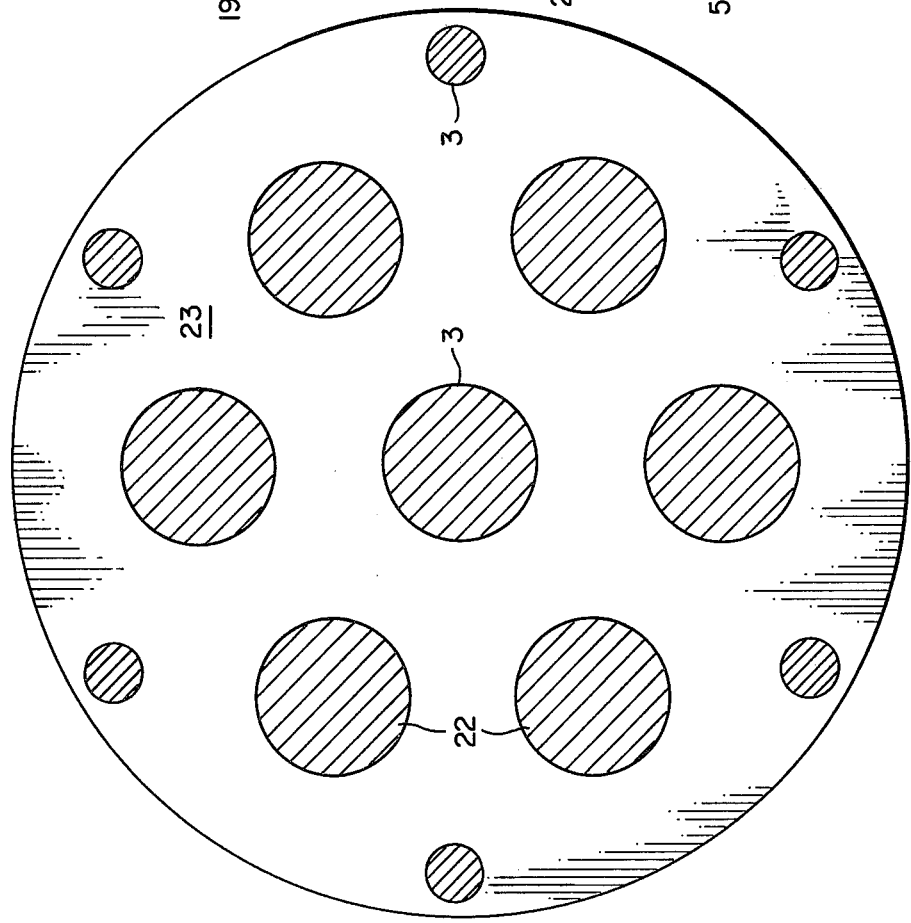
FIG. 8
FIG. 7

FLEXIBLE DIAPHRAGM CONTROLLED VALVE

BACKGROUND OF THE INVENTION

U.S. Pat. No. 4,119,120 describes a fluid switch useful as a sampling device in chromatography systems for switching gaseous or liquid fluid streams between two possible channels. The switch can be employed in two modes. The first as a substitute for two position slider block valves used previously in the art and in the second as a plurality of interconnected switching pairs to provide a plurality of switching actions from a single control fluid switched source.

The aforesaid fluid switch comprises a series of paired enclosures formed by two depressions in a first plate, each depression having an inlet and an outlet and an elastomeric diaphragm covering the depressions. The diaphragm is held in place by a second plate having a first control inlet opposite one depression and a second control inlet opposite one depression and a second control inlet opposite the other depression. A fluid to be switched is connected into the inlets of the first plate in common. By alternatively applying a control fluid to one control inlet and then the other of the second plate, the fluid to be switched is switched from one inlet to the other by the diaphragm alternatively being deformed into one depression and then the other by the control fluid so as to seal the inlet and outlet and thereby block the flow of fluid therethrough from the inlet. Thus, the paired switch valves operate in series and when arranged in multiple arrays flow can be directed to one or the other chambers in each pair but won't proceed from one pair to any other.

A similar multiport flexible diaphragm controlled fluid switching valve is described in Italian Pat. No. 603,986, issued Apr. 27, 1960. As was the case with the valve disclosed in U.S. Pat. No. 4,119,120 and discussed above the paired switch valves are linked in series and when any one valve inlet and outlet are closed, by operation of the control diaphragm then flow of fluid is not possible to other switch valve pairs. Additionally, the inlet and outlet channels are bored within the internal portion of the support plate and thus do not provide a low dead volume passage between the valve chambers.

Other flexible diaphragm controlled fluid valve systems are taught in British Pat. No. 977,364, published Dec. 9, 1964; U.S. Pat. No. 3,095,746, issued July 2, 1963 and U.S. Pat. No. 3,057,594, issued Oct. 9, 1962.

SUMMARY

The present invention describes a unique flexible diaphragm actuated, multiport valve, with a continuous low dead volume channel, which is constantly swept during flow. This channel surrounds each port of the valve and permits flow between open ports. It remains unobstructed to flow in any switching configuration. Thus, each port may be independently opened or closed providing access or lack thereof, to that portion of the channel surrounding each port. When two or more ports are independently opened, the valve provides excellent flexibility in its use as a switching fluid flow valve between these independently controlled ports. By fabricating this valve with a double sided configuration, two independent flow patterns can exist at the same time and be switched independently of one another.

A further feature of the valve of the present invention is the fact that with the exception of the minor motion of the diaphragm moving up and down to permit the opening and closing the various ports, there are no moving parts associated with its operation. By use of proper fabrication materials the valve can be fully functional and operational at temperatures exceeding 400° C.

Another feature of a preferred embodiment of the present valve involves the use of diaphragms with preformed bubble configurations located in direct opposing relationship to the peripheral channels around each port so that fluid flow through the channels will continue if other ports are open even when the port in question is in a closed position. The preformed bubble shape in the diaphragm remains elevated in its relaxed position.

DESCRIPTION OF THE DRAWINGS

FIG. 3 is an inside face view of the back plate showing the recesses each of which may connect with an outside pressure source to provide pressure to move the diaphragm down over the port opening.

FIG. 4 is a cross-sectional view of a single port depicting the preformed bubble diaphragm configuration in the relaxed position allowing flow between the port and the surrounding ring channel.

FIG. 7 is a frontal view of the spacer member used in conjunction with the back plate shown in FIG. 6 allowing separation of the diaphragm and the front plate above each port and corresponding surrounding groove.

FIG. 8 is a cross-sectional view of a single port depicting the flat diaphragm and spacer member configuration when the valve port is in the relaxed or open position allowing fluid flow through the port.

DESCRIPTION OF THE PREFERRED EMBODIMENT

The present invention is directed to an improved multiport, flexible diaphragm actuated valve which is suited for use in conjunction with instruments such as gas or liquid chromatographs. The improvements which are incorporated in such valve are made evident by consideration of the accompanying Figures which are discussed in detail below.

Figure 1:
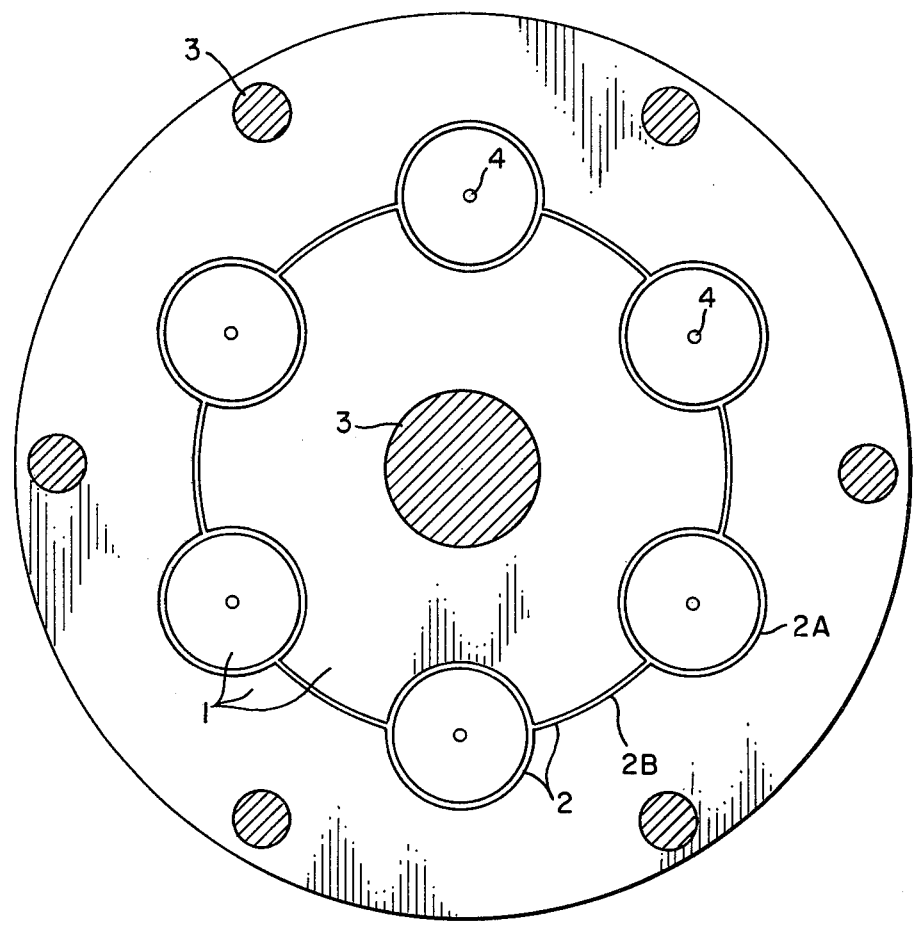
FIG. 1 represents a inside face view of the front base plate of the valve showing the multiple inlet ports with interconnected peripheral channels surrounding each port.

In FIG. 1, a top inside view of the front base plate which forms an integral part of the valve construction is shown. The inside face 1 of the plate is provided with a continuous channel 2 recessed or cut into the plate face and a series of clearance holes containing bolts as a possible method used in holding the valve components together and effecting a gas tight seal where appropriate. The valve plates may also be held together by a weld or a swaged ring around the outside edge. The channel is comprised of peripheral channel portions 2A which surround each of the multiple inlet port opening 4 and interconnecting channel portions 2B which provide a path for fluid flow between adjacent channel rings. The channel is constructed to allow a continuously swept, low dead volume connection between any two or more ports. The cross-sectional area of the channel can be made proportional to the cross sectional area of the inlet ports thus minimizing the dead volume.

The front and back plates of the valve, along with diaphragm, in this instance, are secured by means of bolts passing through bolt holes 3.

In operation each port inlet is independently opened or closed by the application or release of pressure to the back side of the control diaphragm. When the diaphragm is in its open position with respect to one port, flow of fluid is permitted to or from that port through its surrounding continuous channel and may egress through one or more other open ports. Thus, the valve may be used either as a switching valve since any switching combination is possible or when all or nearly all ports are open, as a manifold.

Figure 2:
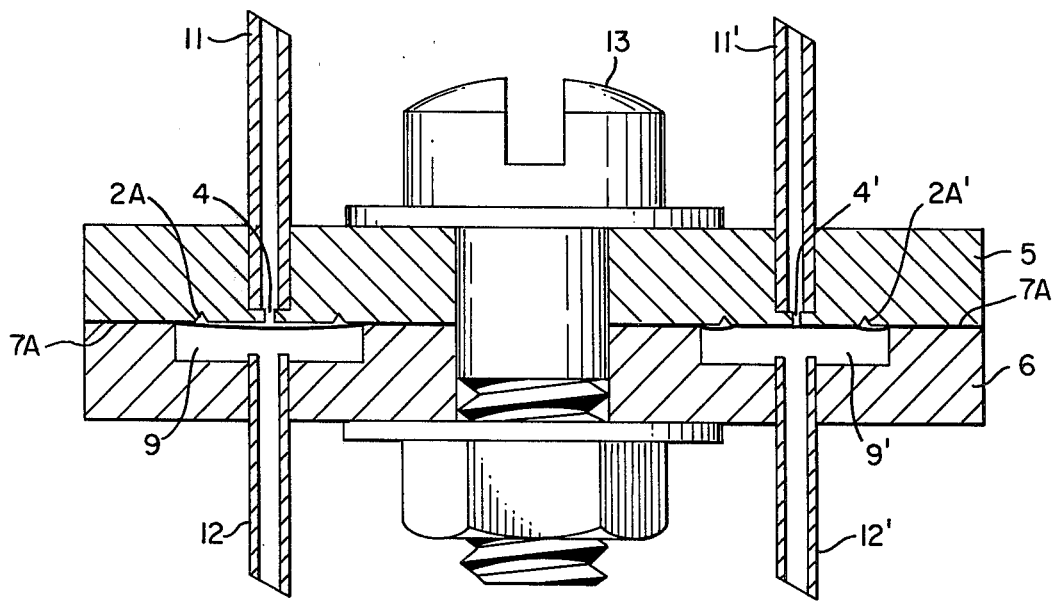
FIG. 2 is a cross-sectional view of the assembled multiport valve bisecting two opposed ports, one in the open and the other in the closed position.

FIG. 2 depicts a cross-sectional view of the multiport valve showing two opposed ports. The front plate 5 and the back plate 6 are secured together by means of holding bolt 13 which passes through the center of the valve through clearance holes in both plates which are in direct registration with each other. The secured plates serve to clamp flexible diaphragm 7A into position between the two plates and into close juxtaposition to the access holes 4 and 4' to ports 11 and 11' respectively. They also serve to maintain a gas tight seal where needed. In the embodiment shown, the diaphragm passing through recess chamber 9, formed in the back plate to permit diaphragm movement, is in the relaxed or open position thus permitting fluid flow in either direction between peripheral channel 2A and port 11 through access hole 4. Use of the preformed bubble shape for diaphragm 7A which remains elevated in its relaxed position facilities such freedom of flow even when pressure is almost zero. Conversely, the portion of the diaphragm passing through the recess chamber 9' is in the pressurized or closed position caused by the application of fluid pressure through pressure port 12' unto the back of the diaphragm which in turn contacts the access hole 4' serving to seal off fluid flow through port 11'.

Due to the relatively small cross-sectional area of channel 2A and 2A', the diaphragm does not enter into the channel when in the pressurized or closed configuration. All recesses on the back plate, including 9 and 9', are independent from one another.

In FIG. 3 a frontal view of the inner side of the back plate is shown. The face surface 14 of the back plate contains an equivalent number of recesses 9 as there are ports on the front plate and such recesses are arranged and constructed to be directly opposed to a corresponding port when the plates are assembled into the finished valve. The pressure port inlets 12 are seen centrally contained in each recess. A number of mounting holes are provided to allow insertion of the bolts used to secure the valve components and to make the device gas tight.

FIG. 4 provides a detailed view of a cross section of one port of the multiport valve. As above front plate 5 and back plate 6 are secured together to form the valve body with diaphragm 7A being centrally disposed between the two plates. The diaphragm is in a preformed bubble configuration and is in a relaxed or open position with respect to access hole 4 of port 11. To achieve this position fluid pressure is vented outwardly from recess 9 as indicated by directional arrow 16A. Fluid flow is now possible between port 11 via access hole 4 and peripheral channel 2A.

Figure 5:
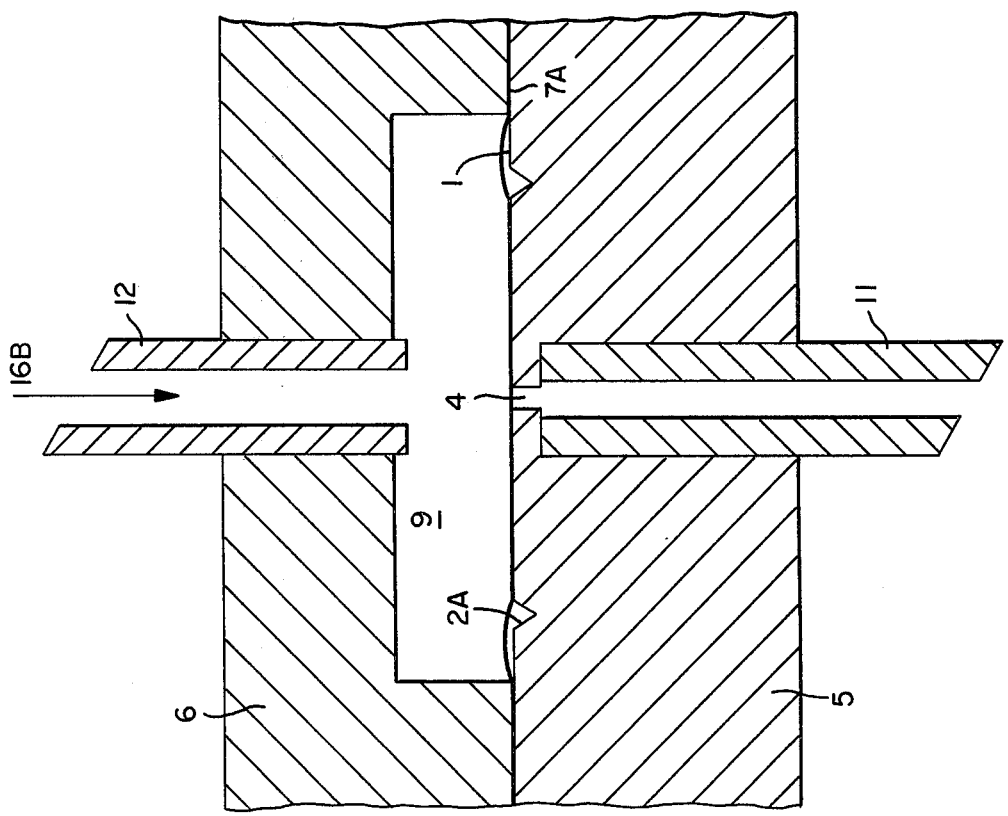
FIG. 5 is a cross-sectional view of a single port depicting the preformed bubble diaphragm configuration in the pressurized or closed position thus preventing flow through the port.

In FIG. 5 the section of the valve shown in the preceding Figure is in the pressurized or closed position. Thus, flow from or to port opening 4 is shut off from channel 2A. Flow through the channel will still continue unobstructed if another two ports are in the open position. To effectuate this closed configuration, pressure fluid, such as compressed air, is directed through pressure port 12 as seen by direction arrow 16B, to pressurize recess 9 so as to cover access hole 4.

Figure 6:
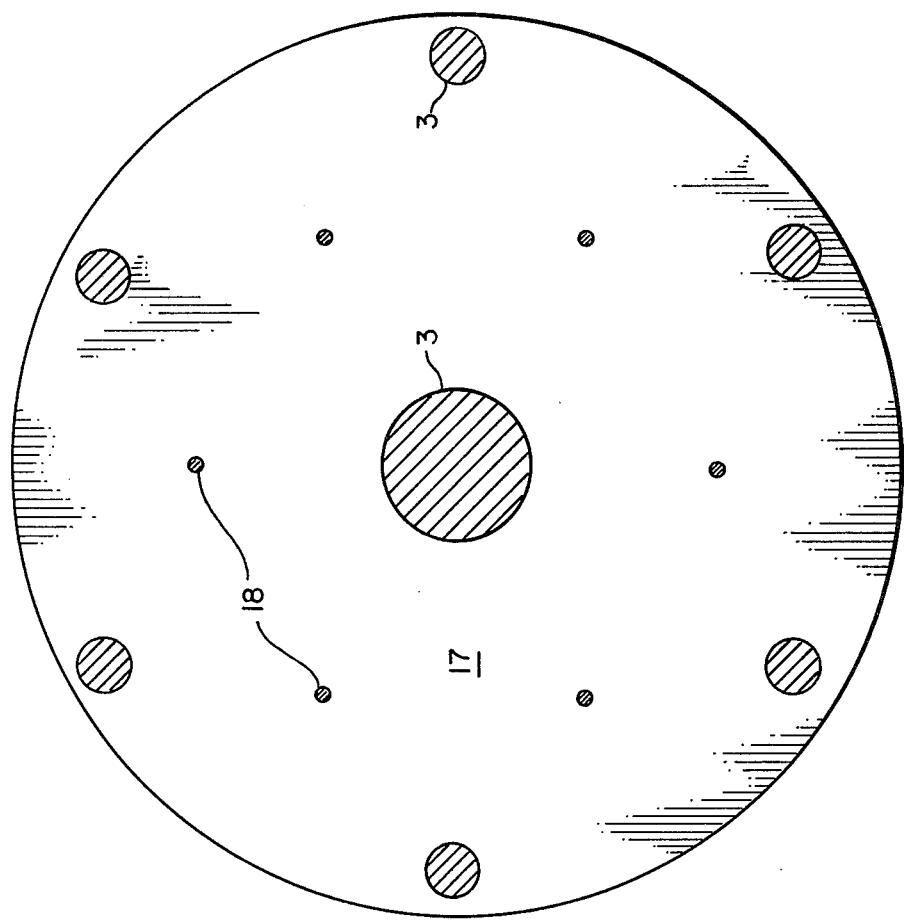
FIG. 6 is an inner face view depicting an alternate back plate construction which can be used in conjunction with a flat diaphragm configuration.

FIG. 6 provides a frontal inside view of a back plate with an alternative pressure port configuration. Ports 18 passing through the plate face 17 are the ports through which pressure fluid flows into the valve. When the valve is assembled the ports 18 are arranged and constructed to be aligned with access holes 4 of the front plate. This alternative back plate configuration is utilized with a flat diaphragm embodiment.

As a further component for use with the flat diaphragm embodiment, FIG. 7 depicts a frontal view of a spacer 23 having mounting holes 3 which register with corresponding holes in the front and back plates in the assembled valve and multiple holes 22 which are aligned with the ports in the assembled valve.

FIG. 8 is a cross-sectional view of a single port section of an assembled valve utilizing a flat diaphragm embodiment. Thus, flat diaphragm 7B is supported between back plate 19 and front plate 5 with the port configuration of the back plate being in the alternative configuration described above in FIG. 6. Spacer 21 is provided to separate the front and back plates and to leave a gap between the diaphragm and the front plate surface 1 when the diaphragm is in a relaxed or unpressurized position. This permits fluid flow between access hole 4 of port 11 and peripheral channel 2A. In this open position, pressure has been vented through pressure port 20 in the direction indicated by arrow 16A.

Figure 9:
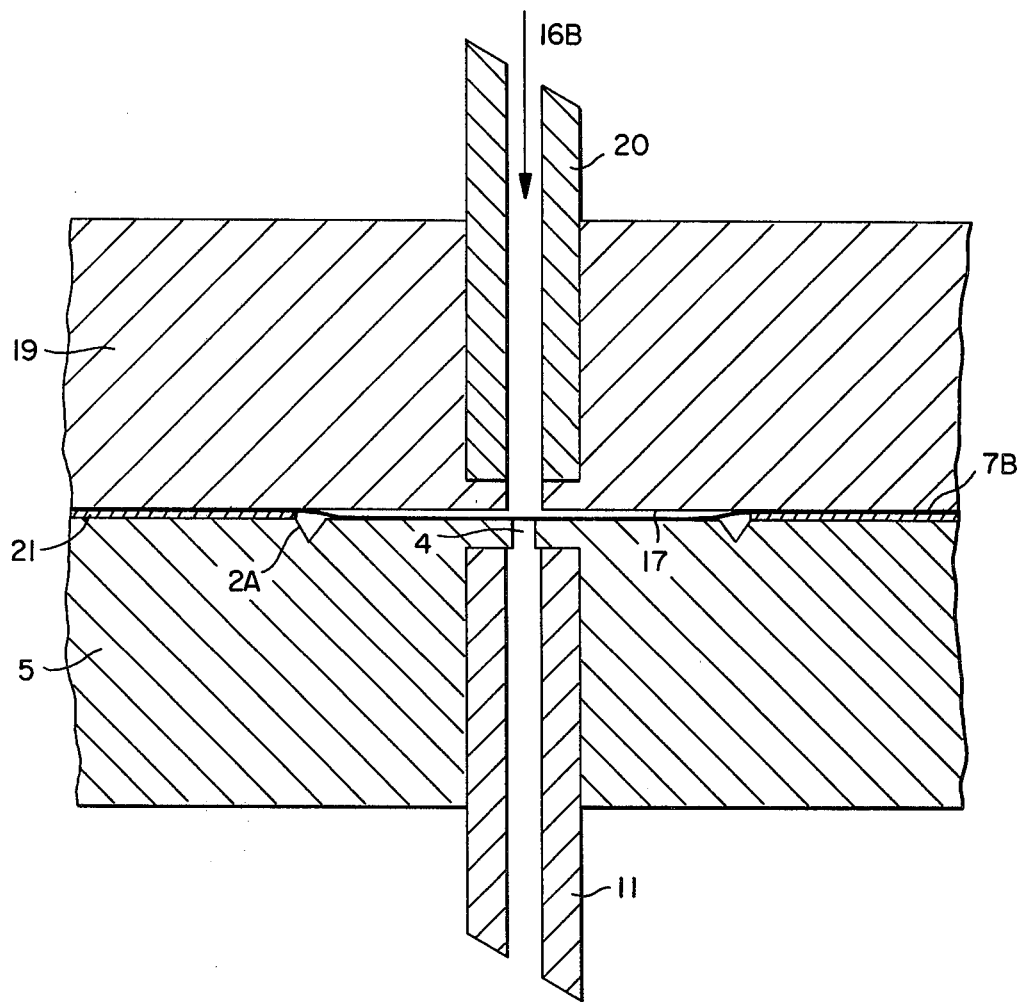
FIG. 9 is a cross-sectional view of a single port depicting the flat diaphragm and spacer member configuration when the valve port is in the pressurized or closed position preventing fluid flow through the port without affecting flow in the peripheral channel.

In FIG. 9 the flat diaphragm embodiment depicted in the previous Figure is shown in the closed position. This is accomplished by introducing pressurized fluid through pressure port 20 in the direction indicated by arrow 16B. The pressure forces diaphragm 7B to seal off the access hole 4 moving the diaphragm away from the face 17 of back plate 19. As before, peripheral channel 2A remains unblocked and fluid flow between any two or more other open ports will continue independently of the closing of the port in this Figure.

Figure 10:
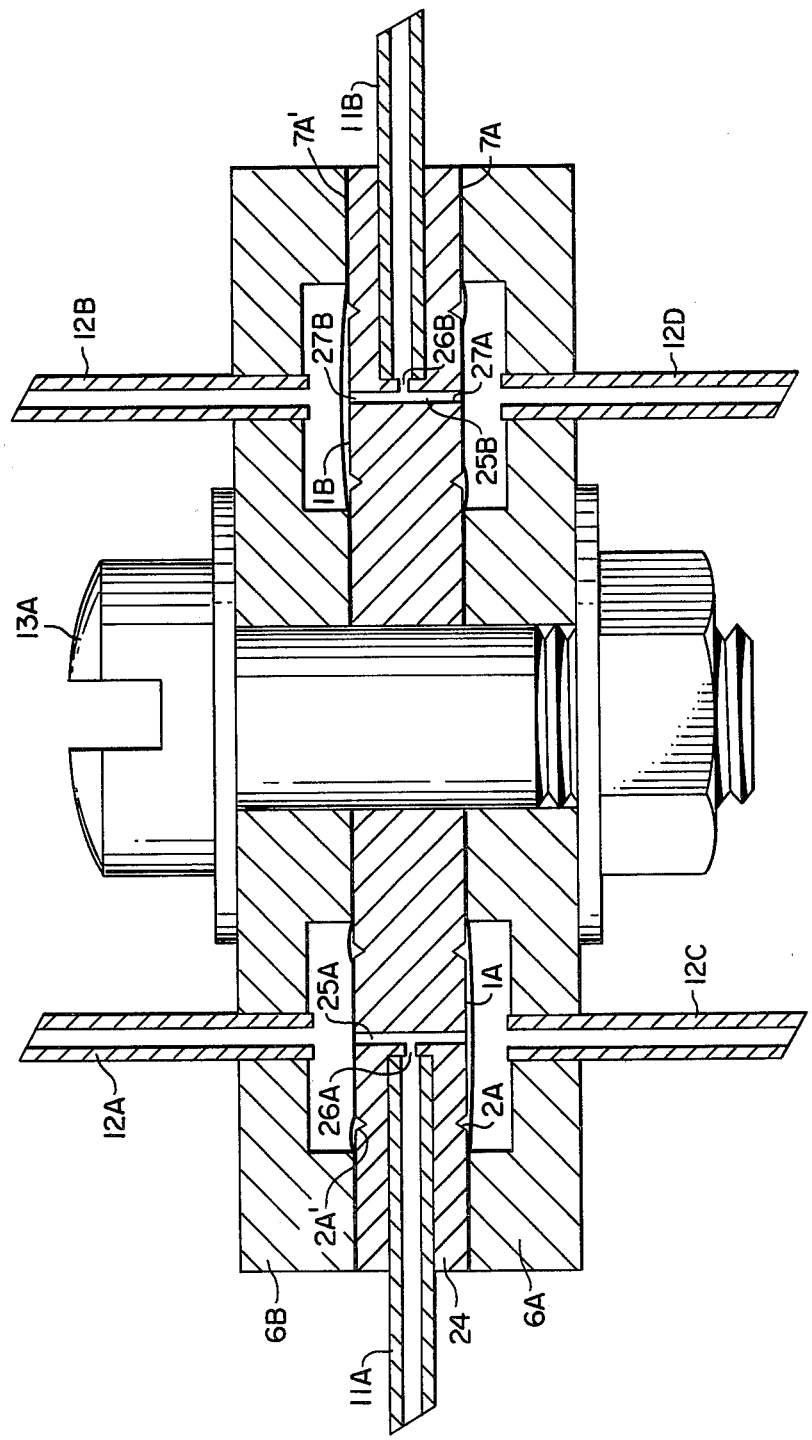
FIG. 10 is a cross-sectional view of the assembled multiport valve in a double sided embodiment which permits two independent flow patterns within the valve to exist simultaneously.

Turning to FIG. 10 there is shown a cross-sectional view of another embodiment of the improved valve of the present invention wherein a double sided valve is shown. In this embodiment bolt 13A secures two back plates 6A and 6B to either side of a double sided front plate 24. The groove channel pattern on each face of plate 24 is identical to that of FIG. 1. The double sided front ports, such as 11A and 11B. Each port is distinguished in having a through channel such as 25A and 25B which opens on both faces of front plate 24 through access holes such as 27A and 27B. The through channels and access holes provide access to fluid flow to or from ports 11A and 11B to the peripheral channels around the ports such as 2A and 2A' depending on whether or nor the respective diaphragms such as 7A or 7A' are in the open or closed position. Each diaphragm is under separate and independent fluid pressure control through pressure fluid inlets such as 12A, 12B, 12C and 12D.

Thus in the embodiment depicted in the subject Figure access hole 27A is closed to fluid flow by the closing action of diaphragm 7A which is acted on by positive fluid pressure introduced through pressure inlet 12D. On the other hand fluid flow to or from port 11B is possible via through channel 25B; access hole 27B the peripheral channel provided on face 1B of front plate 24 since diaphragm 7A' is in the open position. In this embodiment, diaphragm 7A and 7A' are shown in the preformed bubble configuration. Since all ports in the double sided valve embodiment are independently opened or closed, it is possible to establish two independent flow patterns existing simultaneously.

Figure 11:
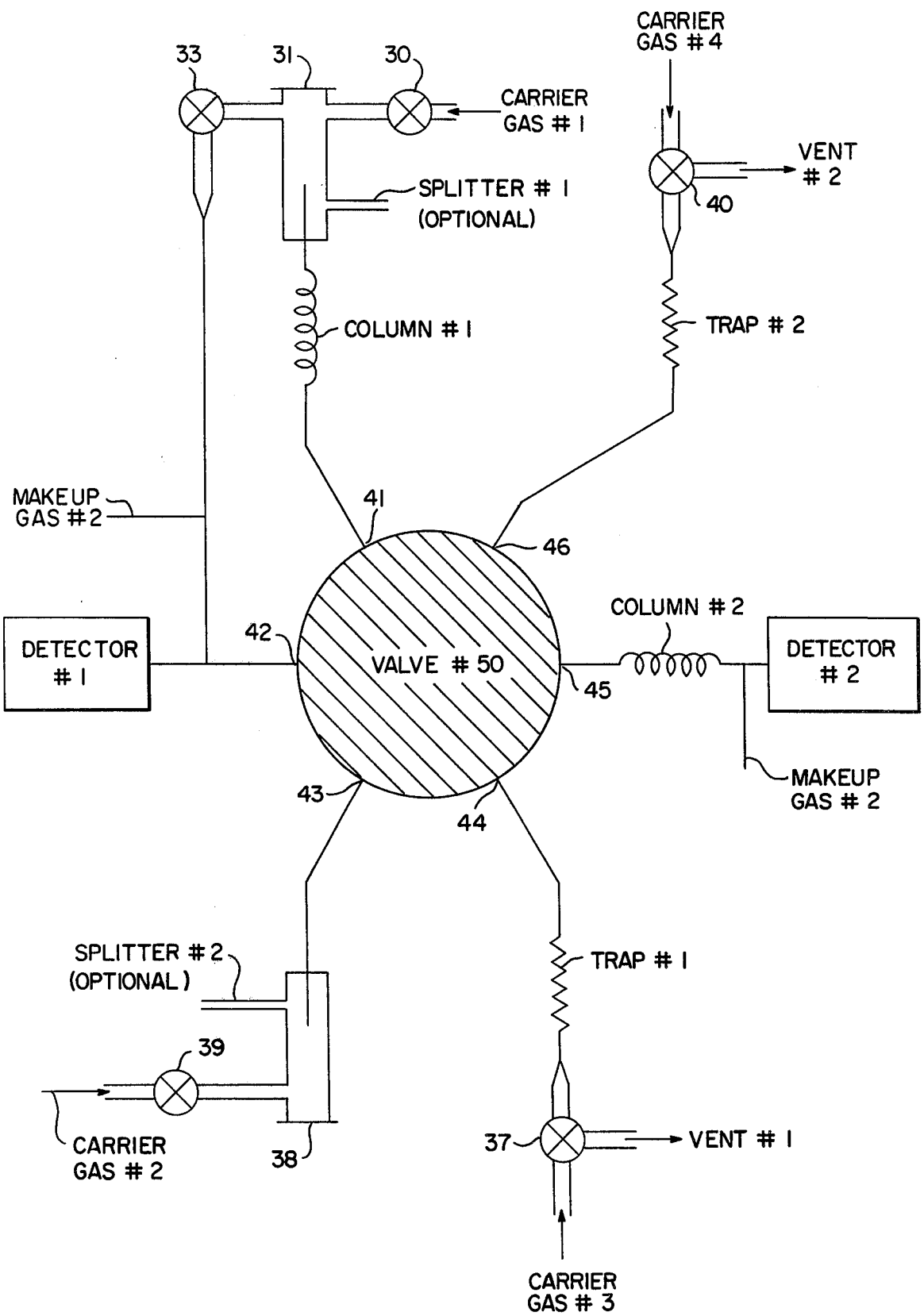
FIG. 11 is a schematic representation of the present multiport valve in a chromatographic system.

FIG. 11 provides a schematic view of a multiport valve of the present invention used in a relatively complex chromatographic system. Thus, for example all of the switching needs for the full operation of this multi-dimensional gas chromatographic system can be met by use of the present invention consisting of, in this instance, a double side 6 port valve whose basic configuration is similar to that shown in FIG. 10. Each port in FIG. 10 enters through the edge of plate 24, branching inside the plate into a "T" formation, each side of which opens out to each face, 1A and 1B, of plate 24. Any or all of the bubble diaphragms adjacent to port openings of both sides of the valve may be actuated completely independent of one another. This can be accomplished by utilizing a pressure source for twelve individually operated solenoid valves. Each solenoid valve is connected to a tube through either backplate. Thus for example, one solenoid valve is connected to tube 12D in FIG. 10. When that solenoid valve is actuated, pressure is allowed to flow through 12D, forcing down the bubbled portion of diaphragm 7A which sits directly over opening 27A. This prevents flow from port 11B through opening 27A. By deactivating the solenoid valve, pressure is released through 12D allowing the bubbled portion of diaphragm 7A above opening 27A to lift off the valve face 1A. Flow may then proceed between opening 27A and its surrounding channel 2A. The twelve solenoid valves may be switched by use of a microprocessor, thus permitting entire switching states to be preprogrammed.

Since the valve is double sided, two flow patterns may exist simultaneously and independently from one another on opposite sides of the valve. One side of the valve will be referred to as side A (analogous to valve face 1A in FIG. 10), the other as side B (analogous to valve face 1B in FIG. 10) in the following discussion.

The chromatographic system shown in FIG. 11, for example, contains two columns, two detectors and two traps. If desired, trap 2 may be replaced by a third detector or a third column if necessary. Each of the columns contains a stationary phase of differing polarity from the other.

The column configuration described above may be used in conjunction with preparative, analytical and/or capillary columns or any combination thereof. Thus, for example:

| First Column | Second Column |
| --- | --- |
| Packed (Analytical or Preparative) or Capillary | Analytical or Capillary |

Therefore, suitable combinations include
    Packed and Capillary or
    Capillary and Capillary Columns The detectors useful in conjunction with the system described above may be any suitable detector used in the chromatographic arts for that purpose, i.e.
    Flame Ionization
    Electron Capture
    Nitrogen/Phosphorus
    Thermal Conductivity
    Coulometric
    Gas Density Balance
    Ultra Violet
    Fluorescence
    Mass Spectrometer
    Infra-Red and the like.

With the use of the valve system depicted in FIG. 11 several switching configurations will be described these are:

1. Column Monitoring. Switching the effluent from Column 1 to Detector 1 and/or from Column 2 to Detector 2.

A sample is injected through injector port 31. It is chromatographed on column 1 using carrier gas supply 1. The separated component bands are detected as they are eluted from the end of column 1 by using detector 1. Carrier gas 1 is fed into the system through open valve 30. Valve 33 is closed. Makeup gas 2 continues to flow into detectors 1 and 2. The end of column 1 is connected to port 41 on multiport valve 50. The input to detector 1 is connected to port 42 on valve 50. The switching configuration for valve 50 is as follows: Ports 41 and 42 are open on Side A of the valve. All other ports on Side A are closed by pressure applied to the backside of the diaphragm over appropriate port openings. Ports 43 and 45 are open on Side B. All other ports on Side B are closed. With this configuration, the output from column 1 is swept through the continuous channel surrounding the opened ports and flows into detector 1 on Side A with a minimal dead volume contribution from the valve. This is particularly important when capillary columns are employed in the system. Simultaneously, carrier gas 2 flowing through open valve 39, is flushing column 2 on Side B.

In a manner similar to that described for column 1 above, column 2 may be independently and simultaneously monitored along with column 1. A sample is injected through injector port 38. Ports 43 and 45 are open on Side B, all other ports on this side are closed. Carrier gas 2 which is fed in through open valve 39, sweeps the injected sample plug through the continuous channel on Side B onto column 2. The chromatographed component bands as they emerge from the exit of column 2 are detected by detector 2. With this configuration, these events can occur while column 1 is being monitored independently if desired, since ports 41 and 42 can be the only ports opened on Side A.

2. Sample Component Transfer

At times, it is desirous to direct some sample component bands which have been chromatographed and are emerging from column 1 to the top of column 2, with minimal distortion or spreading of the bands particularly when capillary columns are used. To accomplish this, at the appropriate time, ports 41 and 45 are opened on Side A. All other ports on this side are closed. Ports 42 and 43 are opened on side B. All other ports on side B are closed. Valve 30 is opened and valve 33 is closed. Make up gas 2 continues to flow into detectors 1 and 2. Flow then proceeds from the outlet of column 1 to the inlet of column 2 on side A of the valve and carrier gas 2 is sweeping detector 1 through side B of the valve. It is noted here that once the desired sample band has been transferred from column 1 to column 2, one may return to the switching configuration used for Column Monitoring with both columns and detectors operated simultaneously and independently.

3. Sample Component Trapping Transfer of Chromatographic Bands From Column 1 to Trap 1 and/or Trap 2

Appropriate narrow bore tubes are used as traps and one side of each tube is connected to ports 44 and 46 of the valve respectively. The other side of the traps may either be vented or be swept with carrier gas depending on the position of valves 37 and 40. The trap, being of low mass, may also be rapidly heated or cooled. For this switching configuration, the trap is cooled so that any sample solutes entering it will condense out on the walls of the trap while the carrier gas is allowed to pass through the trap and exit by means of the vent port via valve 37 and/or 40. To accomplish this, for example, ports 41 and 44 are open on side A of valve 50. All other ports on side A are closed. Ports 43 and 45 are open on side B of the valve. All remaining ports on side B are closed. Valve 37 is switched so that the carrier gas emerging from column 1 is vented through vent 1. In this configuration, the output flow of column 1 enters the inlet of trap 1 through side A of the valve. Column 2 is flushed with carrier gas 2 through side B of the valve. In a similar manner, a different segment of the chromatographic effluent leaving column 1 may be selectively condensed in trap 2. Here, ports 41 and 46 are open on side A of valve 50. All other ports on side A are closed. Ports 43 and 45 are open on side B of the valve. All remaining ports on side B are closed. Valve 40 is switched so that the carrier gas emerging from column 1 is vented through vent 2.

4. Transfer of Sample Components from Trap 1 and/or Trap 2 to Column 2

After a selected sample component or components have been condensed on the cooled walls of trap 1, these components may be released from the walls by a rapid heating of trap 1. Port 44 and 45 on side B of valve 50 are opened. All other ports on side B are closed. Valve 37 is switched so that carrier gas 3 flows into trap 1 as trap 1 is being heated. Ports 41 and 42 on side A of valve 50 are open. All remaining ports on side A are closed. In this switching pattern, the output of trap 1 is sent into column 2 through side B. Detector 1 is connected to the output of column 1 through side A.

Similarly, other components that have been selectively condensed in trap 2 may be transferred to column 2. Thus, after trapping of the chromatographed band(s) in trap 2, ports 45 and 46 on Side B of valve 50 are opened. All other ports on side B are closed. Valve 40 is switched so that carrier gas 4 flows into trap 2 as trap 2 is being heated. Ports 41 and 42 on Side A of valve 50 are open. All remaining ports on Side A are closed. In this switching pattern, the output of trap 2 is sent into column 2 through side B. Detector 1 is connected to the output of column 1 through side A.

5. Back flushing of certain sample components still residing on Column 1

Ports 41 and 43 are open on side A of valve 50. All other ports on side A are closed. Valve 30 is closed and valve 33 is open. Thus the output backflushed out of column 1 will flow through and be sensed by detector 1. Ports 43 and 45 are open on side B of the valve. All other ports on side B are closed. Thus, in this configuration, with valve 39 open, carrier gas 2 backflushes column 1 through side A and forward flushes column 2 through side B. (Column 2 may also be flushed with carrier gas 3 through trap 1 instead of utilizing carrier gas 2, i.e., port 44 is open, port 43 is closed on side B, and valve 37 is open connecting carrier gas 3 to trap 1.

6. Solvent flushing

In this embodiment, the sample is injected into the first injector 31 and moves onto column 1 to be chromatographed. At this point, valve 50 is in switching configuration described under Column Monitoring. When the solvent peak is detected in detector 1, valve 50 is then switched to the solvent flushing mode. Ports 43 and 42 on side B of the valve are open and all other ports on side B are closed. Ports 41 and 45 are open opn side A of the valve (trap 1 may be open to flow instead of column 2). All other ports on side A are closed. Also port 41 may be completely closed after detection of the solvent peak. Carrier gas 2 is switched to flush the solvent peak from detector 1. (It can also be used to flush column 2). Then port 4 on side A of the valve may be opened so that chromatographic bands emerging from column 1 devoid of most if not all of the solvent can then either be detected in detector 1, and/or trapped in the cooled trap 1, and/or transferred to column 2 using switching configurations 1, 3 or 2 respectively as explained above.

Certainly many more switching possibilities other than those mentioned above are possible with the system shown in FIG. 11.

The fluid pressure actuating the diaphragms can be gas or liquid. Also mechanical actuation is possible in extremely high pressure applications such as liquid chromatography. For fluid actuation, the pressure can be supplied from any convenient source and switched through a multiple solenoid manifold, to each pressure fluid inlet in the multiport valve.

The pressure fluid used for controlling the diaphragm position is preferably a gas, such as an inert gas, for example, argon, helium, nitrogen, carbon dioxide, compressed air or any other gas conventionally utilized in valve control. The gas can be provided from any convenient source preferably a gas cylinder and distributed through a multiple solenoid valved manifold to each pressure fluid inlet in the multiport valve.

Materials for use in construction of the valve body include metals such as stainless steel or a thermosetting, chemically inert, and heat resistant plastic such as Kel-F (a polymer of chlorotrifluoroethylene). The diaphragm may be produced from a thin, flexible, chemically-inert and heat resistant plastic such as Mylar (a polyester) film), Teflon (a polytetrafluorethylene film), polyimide, Kalrez (a perfluoroelastomer) and the like; or silicone rubber either alone or coated with said plastic materials; or a thin metallic sheet either alone or coated or laminated with said plastic materials. For use at temperatures of 250° C. or above, an all metallic construction of the valve body and diaphragm is preferred.

The introduction of the preformed bubbles in the diaphragm in positions registering with each port can be readily accomplished by molding or stamping the bubbles into the diaphragm film prior to fabrication into the valve.

Suitable carrier gases for use in the instant valves include the inert gases such as helium, nitrogen, argon and the like or hydrogen.

While the valve of the invention has been described utilizing up to six separate ports it is within the scope of the invention to employ fewer or greater numbers of ports. Similarly while the ports have been shown in circular configuration they may be used in any convenient geometric relationship without materially affecting performance. Furthermore, the peripheral channels can be interconnected by direct pathways instead of or in addition to the circumferential connecting between adjacent ports depicted herein.

Thus, the valve of the present invention is seen to provide a number of advantages in construction and operation as follows:

1. It is a very low dead volume valve due to presence of a continuous channel with a small cross sectional area which is completely and continuously swept when two or more ports are opened.

2. The shape of the diaphragm contributes negligible dead volume between the port opening and its surrounding channel ring.

3. With the exception of the small excursion of the diaphragm moving up and down, there are no moving parts associated with the operation of this valve. Slider or rotor parts are absent. Under these circumstances certain materials, for example, gold, which would ordinarily seize upon sliding, can be readily utilized in the construction of the valve.

4. The valve can be fabricated from materials which permit it to be fully functional and operational at temperatures exceeding 400° C.

5. The valve surfaces, if fabricated from metal, for example, may be rendered to be relatively inert chemically by the application of an appropriate film of a relative inert material such as gold deposited on those surfaces exposed to sample fluid or gas.

6. The configuration of the valve and its dimensions may be so arranged thereby permitting it to operate in most if not all areas of chromatography. For example, on the one hand, with relatively small effluents from capillary columns which may be efficiently and effectively switched and transferred to different detectors, different columns, traps, collecting devices, and to other instruments, for example, such as a mass spectrometer. Similarly, relatively large effluents from analytical, semi preparative, or preparative chromatographic columns can also be efficiently and effectively handled in a like manner by the utilization of the basic configuration of the valve with small changes in the size of the continuous channel, the port openings and the diaphragm and its surrounding area.

7. By the appropriate choice of diaphragm material and thickness, and the appropriate choice of adequate shut off pressure, the valve can be made to function at pressures extending up to 2000–5000 psi, if necessary.

8. The configuration of the valve permits independent and rapid switching to the on or off positions of any combination of ports within a fraction of a second. The switching mechanism lends itself to the automated control of this function by, for example, the use of microprocessor or computer controlled solenoid valve or appropriate fluidic control systems.

9. The valve can be made relatively small and of low mass so that if it is used in chromatography, where the temperature of the chromatographic system may be raised or lowered rapidly, the temperature of the valve will not appreciably lag behind that of the surrounding media.

10. The diaphragm of this valve may be actuated by a number of methods, for example, force applied by fluid pressure or mechanical means.

11. The valve can be used with minor changes to effectively operate under vacuum and be used for example in mass spectrometry or combined gas chromatography-mass spectrometry instruments.

12. The working principles of the present invention permits many forms of the valve to be realized. The two described herein are a single sided and double sided six port valve.

I claim:

1. An improved fluid pressure controlled diaphragm actuated multiport valve comprising:
   (a) a first plate having a multiplicity of control fluid inlet means passing through said first plate each of said control fluid inlet means being connectable to a source of control fluid under pressure, and under independent pressure control;
   (b) a second plate assembled adjacent said first plate having a multiplicity of fluid conduct means passing through said second plate, each of said fluid conduit means opening opposite a corresponding control fluid inlet means in said first plate said second plate further having a multiplicity of operatively interconnected, low dead volume fluid channel means on its inner surface peripherally surrounding each of said fluid conduit means;
   (c) a flexible diaphragm means disposed between said first plate and said second plate when said plates are assembled adjacent one another, said diaphragm means being so arranged and constructed as to seal any fluid conduit means to fluid flow when said corresponding control fluid inlet means is open to control fluid under pressure, wherein said channel means are in independent operative fluid flow connection with each said fluid conduit means when said diaphragm is not in sealing position with respect to said fluid conduit means and are not in operative fluid flow connection with each said fluid conduit means when said diaphragm is in sealing position, wherein further said channel means are so arranged and constructed to maintain operative fluid flow connection between any of said fluid conduit means which are not sealed; and
   (d) means for holding said first plate, said second plate and said diaphragm in assembled adjacent relationship.

2. The improved valve of claim 1 wherein said diaphragm contains preformed bubble members arranged to correspond in position to each of said fluid conduit means.

3. The improved valve of claim 1 wherein two of said first plates are provided, one on each side of said second plate and said fluid conduit means in said second plate are each bifurcated to provide an opening at each side of said second plate, each of said openings being in corresponding positions to a control fluid inlet means in said first plates to allow independent sealing or opening of said openings by said diaphragm to thus provide a doubly faced valve.

4. A chromatograph system comprising the improved valve of claim 3, multiple chromatographic columns each having an inlet and an outlet and multiple detector means wherein a corresponding number of said fluid conduit means are each operatively connected to each of said outlets and a corresponding number of other said fluid conduit means are each operatively connected to each said detector means.

5. The improved valve of claim 1 wherein said fluid conduit means are in a circular configuration within said second plate and said fluid channel means are circularly disposed around the periphery of each said fluid conduit means.

6. The improved valve of claim 1 wherein said valve components and diaphragm are metallic thereby allowing operation at temperatures in excess of 250° C.

7. A chromatograph system comprising the improved valve of claim 1, a chromatographic column having an inlet and an outlet and a detector means wherein at least one of said fluid conduit means is operatively connected to said outlet of said chromatographic column and at least one other of said fluid conduit means is operatively connected to said detector means.

* * * * *